US005750566A

United States Patent [19]

Monn et al.

[11] Patent Number: 5,750,566
[45] Date of Patent: May 12, 1998

[54] SYNTHETIC EXCITATORY AMINO ACIDS

[75] Inventors: James A. Monn; Darryle D. Schoepp, both of Indianapolis, Ind.

[73] Assignee: Eli Lilly and Company, Indianapolis, Ind.

[21] Appl. No.: 496,643

[22] Filed: Jun. 29, 1995

Related U.S. Application Data

[63] Continuation-in-part of Ser. No. 337,349, Nov. 10, 1994, abandoned, which is a continuation-in-part of Ser. No. 289,957, Aug. 12, 1994, abandoned.

[51] Int. Cl.$^6$ ............................................. A61K 31/21
[52] U.S. Cl. ........................... 514/510; 514/561; 560/119; 562/501
[58] Field of Search ......................... 560/119; 562/501; 514/510, 560, 561

[56] References Cited

U.S. PATENT DOCUMENTS 3,532,744  10/1970  Fletcher et al. .
3,704,312  11/1972  Russell et al. .
3,746,495   7/1973  Malis et al. .

FOREIGN PATENT DOCUMENTS

WO 95/15940  6/1995  European Pat. Off. .

OTHER PUBLICATIONS

G. Costantino, et al., "Definition of a Pharmacophore for the Metabotropic Glutamate Receptors Negatively Linked to Adenylyl Cyclase", *Bioorganic & Medicinal Chemistry*, 1, 259–265 (1993).

J. Greenstein et al, "Chemistry of the Amino Acids", John Wiley & Sons, Inc (New York), 6, 2559–2567 (1961).

D.D. Schoepp, et al., *European Journal of Pharmacology*, vol. 207, 1991, pp. 351–353.

U.S. application No. 08/500,303, filed Jul. 10, 1995.
U.S. application No. 08/496,710, filed Jun. 29, 1995.
U.S. application No. 08/496,642, filed Jun. 29, 1995.

Y. Nakagawa et al., "(2S, 3S, 4S) α-(Carboxycyclopropyl)-glycine is a novel agonist of metabotropic glutamate receptors," *European J. Pharmacology*, 184, 205–206 (1990).

Y. Hayashi et al., "Agonist analysis of 2-(Carboxycyclopropyl) glycine isomers for cloned metabotropic glutamate receptor subtypes expressed in Chinese hamster ovary cells," *Br. J. Pharmacol.*, 107, 539–543 (1992).

H. Shinozaki and M. Ishida, "Recent Advances in the Study of Glutamate Receptor Agonists," *Asia Pacific J. of Pharmacol.*, 6, 293–316 (1991).

F. Nicoletti et al., "(2s,1'$_R$,2'$_R$,3'$_R$) -2-(2,3-Dicarboxycyclopropyl) glycine enhances quisqualate-stimulated inositol phospholipid hydrolysis in hippocampal slices," *Eur. J. Pharmacol. -Molecular Pharmacol. Section*, 245, 297–298 (1993).

M. Ishida et al., "A potent metabotropic glutamate receptor agonist: electrophysiological actions of a conformationally restricted glutamate analogue in the rat spinal cord and Xenopus oocytes," *Brain Res.*, 537, 311–314 (1990).

M. Ishida et al., "A novel metabotropic glutamate receptor agonist: marked depression of monosynaptic excitation in the newborn rat isolated spinal cord," *Br. J. Pharmacol.*, 109, 1169–1177 (1993).

V. Bruno et al., "Protective effect of the metabotropic glutamate receptor agonist, DCG-IV, against excitotoxic neuronal death," *Eur. J. Pharmacol.*, 256, 109–112 (1994).

H. Kaba et al., "Induction of an Olfactory Memory by the Activation of a Metabotropic Glutamate Receptor," *Science*, 265, 262–264 (Jul. 8, 1994).

D.E. Jane et al., "Actions of two new antagonists showing selectively for different sub-types of metabotropic glutamate receptor in the neonatal rat spinal cord," *Br. J. Pharmacol.*, 112, 809–816 (1994).

F. Nicoletti et al., "Effect of Metabotropic Glutamate Receptor Agonists on Excitotoxic or Apoptotic Neuronal Degeneration," *Neuropschychopharmacology*, 10 (3S), 623S (1994).

*Primary Examiner*—Michael L. Shippen
*Attorney, Agent, or Firm*—Martin A. Hay; David E. Boone; James P. Leeds

[57] ABSTRACT

The present invention provides novel compounds that affect certain excitatory amino acid receptors, and are useful in the treatment of neurological disorders and psychiatric disorders.

13 Claims, No Drawings

SYNTHETIC EXCITATORY AMINO ACIDS

This application is a continuation-in-part of Application Ser. No. 08/337,349, now abandoned, filed Nov. 10, 1994, which is a continuation-in-part of Application Ser. No. 08/289,957, filed Aug. 12, 1994, now abandoned.

BACKGROUND OF THE INVENTION

In the mammalian central nervous system (CNS), the transmission of nerve impulses is controlled by the interaction between a neurotransmitter, that is released by a sending neuron, and a surface receptor on a receiving neuron, causing excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, emotional states and sensory perception.

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in cAMP formation, and changes in ion channel function. Schoepp and Conn, *Trends in Pharmacol. Sci.*, 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

The metabotropic glutamate receptors are a highly heterogeneous family of glutamate receptors that are linked to multiple second-messenger pathways. Generally, these receptors function to modulate the presynaptic release of glutamate, and the postsynaptic sensitivity of the neuronal cell to glutamate excitation. The metabotropic glutamate receptors (mGluR) have been pharmacologically divided into two subtypes. One group of receptors is positively coupled to phospholipase C, which causes hydrolysis of cellular phosphoinositides (PI). This first group are termed PI-linked metabotropic glutamate receptors. The second group of receptors is negatively coupled to adenyl cyclase, which prevents the forskolin-stimulated accumulation of cyclic adenosine monophosphate (cAMP). Schoepp and Conn, *Trends Pharmacol. Sci.*, 14, 13 (1993). Receptors within this second group are termed cAMP-linked metabotropic glutamate receptors. Agonists of the cAMP-linked metabotropic glutamate receptors should be useful for the treatment of acute and chronic neurological conditions and psychiatric conditions.

Compounds have recently been discovered that affect metabotropic glutamate receptors, but have no effect on ionotropic glutamate receptors. (1S,3R)-1-Aminocyclopentane-1,3-dicarboxylic acid (1S,3R-ACPD) is an agonist of PI-linked and cAMP-linked metabotropic glutamate receptors. Schoepp, Johnson, True, and Monn, *Eur. J. Pharmacol.*, 207, 351 (1991); Schoepp, Johnson, and Monn, *J. Neurochem.*, 58, 1184 (1992). (2S,3S,4S)-2-(carboxycyclopropyl)glycine (L-CCG-I) was recently described as a selective cAMP-linked metabotropic glutamate receptor agonist; however, at higher concentrations, this compound has activity at PI-linked metabotropic receptors. Nakagawa, et al., *Eur. J. Pharmacol.*, 184, 205 (1990); Hayashi, et al., *Br. J. Pharmacol.*, 107, 539 (1992); Schoepp et al., *J. Neurochem.*, 63., page 769–772 (1994).

SUMMARY OF THE INVENTION

The present invention provides compounds that selectively affect the negatively-coupled cAMP-linked metabotropic glutamate receptors. More specifically, the present invention relates to compounds of the formula

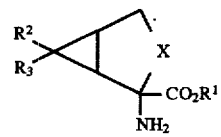

wherein:

X is $(CH_2)_n$;

$R^2$ is $CO_2R^4$ and $R^3$ is hydrogen, or $R^2$ is hydrogen and $R^3$ is $CO_2R^4$;

$R^1$ and $R^4$ are independently hydrogen, $C_1$–$C_{10}$ alkyl, $C_2$–$C_{10}$ alkenyl, aryl, or arylalkyl; and n is 1;

or a pharmaceutically-acceptable salt thereof.

The present invention also provides pharmaceutical formulations comprising a compound of formula I in combination with one or more pharmaceutically-acceptable carriers, diluents, or excipients.

Further aspects of the present invention include a method for affecting the cAMP-linked metabotropic glutamate receptors, as well as methods for treating a neurological disorder or a psychiatric disorder that has been linked to the excitatory amino acid receptors, which comprises administering a compound of formula I. Examples of neurological disorders that are treated with a formula I compound include cerebral deficits subsequent to cardiac bypass surgery and grafting, cerebral ischemia (e.g. stroke and cardiac arrest); spinal cord trauma; head trauma; Alzheimer's Disease; Huntington's Chorea; amyotrophic lateral sclerosis; AIDS-induced dementia; muscular spasms; migraine headaches; urinary incontinence; convulsions; perinatal hypoxia; hypoglycemic neuronal damage; drug tolerance, withdrawal, and cessation (i.e. opiates, benzodiazepines, nicotine, cocaine, or ethanol); smoking cessation; ocular damage and retinopathy; cognitive disorders; idiopathic and drug-induced Parkinson's Disease; emesis; brain edema; chronic pain; sleep disorders; Tourette's syndrome; attention deficit disorder; and tardive dyskinesia. Examples of psychiatric disorders that are treated with a formula I compound include schizophrenia, anxiety and related disorders (e.g. panic attack and stress-related disorders), depression, bipolar disorders, psychosis, and obsessive compulsive disorders.

The present invention also provides compounds that are useful for the synthesis of the formula I compounds. Specifically, the present invention relates to compounds of the formula

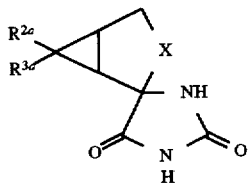

wherein:

X is $(CH_2)_n$;

n is 1;

$R^{2a}$ is $CO_2R^{4a}$ and $R^{3a}$ is hydrogen, or $R^{2a}$ is hydrogen and $R^{3a}$ is $CO_2R^{4a}$; and $R^{4a}$ is hydrogen or a carboxy protecting group; and salts thereof.

The present invention also provides a process for producing a compound of formula I, or a pharmaceutically salt thereof, which comprises:

(1) hydrolyzing a compound of the formula

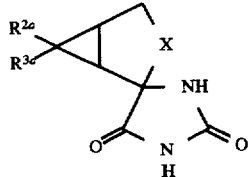

wherein:

X is $(CH_2)_n$;

n is 1;

$R^{2a}$ is $CO_2R^{4a}$ and $R^{3a}$ is hydrogen, or $R^{2a}$ is hydrogen and $R^{3a}$ is $CO_2R^{4a}$; and $R^{4a}$ is hydrogen or a carboxy protecting group;

(2) reacting a compound of the formula

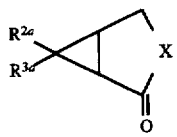

wherein X, $R^{2a}$, and $R^{3a}$ are as defined above, with an alkali metal cyanide and an ammonium salt, and hydrolyzing the resulting intermediate as in (1) above; or (3) hydrolyzing a compound of the formula

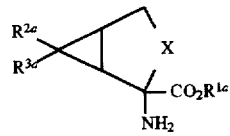

wherein $R^{1a}$ is a carboxy protecting group and X, $R^{2a}$, and $R^{3a}$ are as defined above; and (4) optionally removing the carboxy protecting group; and (5) optionally esterifying one or both carboxyl groups; and (6) optionally separating the diastereomers and/or resolving the enantiomers; and (7) optionally preparing a pharmaceutically-acceptable salt of the formula I compound.

DETAILED DESCRIPTION OF THE INVENTION

The term "$C_1$–$C_{10}$ alkyl" represents a straight, branched, or cyclic alkyl chain having from one to ten carbon atoms. Typical straight or branched $C_1$–$C_{10}$ alkyl groups include methyl, ethyl, n-propyl, isopropyl, n-butyl, isobutyl, sec-butyl, t-butyl, n-pentyl, isopentyl, neopentyl, n-hexyl, 2-methylpentyl, 3-methylpentyl, 4-methylpentyl, 2,2-dimethylbutyl, 2,3-dimethylbutyl, 3,3-dimethylbutyl, heptyl, n-octyl, 2,2-dimethylhexyl, 2,5-dimethylhexyl, 2-methylheptyl, 4-methylheptyl, 2,2,4-trimethylpentyl, 2,3,4-trimethylpentyl, nonyl, 3,5,5-trimethylhexyl, decyl, 3,7-dimethyloctyl, and the like. The term "$C_1$–$C_{10}$ alkyl" includes within it the terms "$C_1$–$C_{16}$ alkyl" and "$C_1$–$C_4$ alkyl". Typical cyclic alkyl groups include cyclopropyl, cyclobutyl, cyclopentyl, cyclohexyl, cycloheptyl, and the like. Typical $C_1$–$C_6$ alkyl groups include methyl, ethyl, n-propyl, isopropyl, n-butyl, isobutyl, sec-butyl, t-butyl, n-pentyl, isopentyl, neopentyl, and n-hexyl.

The term "$C_2$–$C_{10}$ alkenyl" represents straight or branched unsaturated alkyl chains having from two to ten carbon atoms, and having one or more carbon-carbon double bond, such as, dienes and trienes. This group also includes both E and Z isomers. Representative radicals for this group include vinyl, allyl, allenyl, 1-butenyl, 2-butenyl, 2-methyl-1-propenyl, 3-butenyl, 2-methyl-2-propenyl, butadienyl, 1-pentenyl, 2-pentenyl, 2-methyl-2-butenyl, 4-pentenyl, 3-methyl-2-butenyl, 3-methyl-1,2-butadienyl, 3-hexenyl, 2-hexenyl, 4-methyl-3-pentenyl, 4-hexenyl, 5-hexenyl, 3-methyl-1-penten-3-yl, 4-methyl-3-pentenyl, 6-methyl-5-heptene-2-yl, 7-octenyl, 1-octen-3-yl, 3-nonenyl, 2,4-dimethyl-2,6-heptadienyl, 3,7-dimethyl-6-octenyl, 5-decenyl, 9-decenyl, 2,6-dimethyl-7-octenyl, and the like. The term "$C_2$-$C_{10}$ alkenyl" includes within it the term "$C_2$-$C_6$ alkenyl".

The phrase "stereoisomeric compound" represents an optical isomer of a Formula I compound. Representative stereoisomeric compounds include the 1S,2S,5R,6S isomer, 1R,2R,5S,6R isomer, the 1S,2R,5R,6S isomer, the 1R,2S,5S,6R isomer, the 1S,2S,5R,6R isomer, the 1R,2R,5S,6S isomer, the 1S,2R,5R,6R isomer, and the 1R,2S,5S,6S isomer.

The phrase "diastereomeric compound" represents a mixture of two non-superimposable stereoisomers of a Formula I compound. Representative diastereomeric compounds include the 1SR,2SR,5RS,6SR mixture, the 1SR,2RS,5RS,6SR mixture, the 1SR,2SR,5RS,6RS mixture, and the 1SR, 2RS,5RS,6RS mixture. The preferred diastereomeric compound is the 1SR,2SR,5RS,6SR mixture. The preferred enantiomer is 1S, 2S, 5R, 6S.

The term "carboxy protecting group" as used herein refers to one of the ester derivatives of the carboxylic acid group commonly employed to block or protect the carboxylic acid group while reactions are carried out on other functional groups. The protection of carboxylic acid groups is generally described in McOmie, Protecting Groups in Organic Chemistry, Plenum Press, NY, 1973; and Greene and Wuts, Protecting Groups in Organic Synthesis, 2nd. Ed., John Wiley & Sons, NY, 1991. Examples of such carboxy protecting groups include methyl, ethyl, methoxymethyl, methylthiomethyl, triphenylmethyl, benzyl, 4-nitrobenzyl, 4-methoxybenzyl, 3,4-dimethoxy-benzyl, 2,4-dimethoxybenzyl, 2,4,6-trimethoxybenzyl, 2,4,6-trimethylbenzyl, benzhydryl, t-butyl, t-amyl, trityl, trimethylsilyl, t-butyldimethyl-silyl, allyl, 1-(trimethylsilylmethyl)-prop-1-en-3-yl, and the like. Particularly preferred carboxy protecting groups are ($C_1$–$C_6$) alkyl groups such as methyl and ethyl. The term "protected carboxy" refers to a carboxylic acid group having a carboxy protecting group.

The term "nitrogen protecting group" as used herein refers to substituents on amino groups that are commonly employed to block or protect the amino functionality while reactions are carried out in other functional groups. The protection of amino groups is generally described in McOmie, Protecting Groups in Organic Chemistry; Plenum Press, NY, 1973, and Greene and Wuts, Protecting Groups in Organic Synthesis, 2nd. Ed., John Wiley & Sons, NY, 1991. Examples of nitrogen protecting groups include benzyl, t-butyl, allyl, triphenylmethyl, t-butyldimethylsilyl, triphenylsilyl, formyl, trityl, phthalimido, trichloroacetyl, chloroacetyl, phthaloyl, 2-nitrophenoxyacetyl, benzyloxycarbonyl, methoxycarbonyl, 2-methylbenzyloxycarbonyl, t-butoxycarbonyl, allyloxycarbonyl, 2,2,2-trichloroethoxycarbonyl, and the like. The term "protected amino" refers to a primary or secondary amine having a nitrogen protecting group.

The term "$C_1$–$C_4$ alkoxy" represents groups such as methoxy, ethoxy, n-propoxy, isopropoxy, n-butoxy, sec-butoxy, and t-butoxy. The term "halogen" refers to fluoro, chloro, bromo, and iodo.

The term "alkoxycarbonyl", means a carboxyl group having a $C_1$–$C_6$ alkyl group attached to the carbonyl carbon through an oxygen atom. Representatives of this group include methoxycarbonyl, ethoxycarbonyl, n-propoxycarbonyl, n-butoxycarbonyl, t-butoxycarbonyl, and the like. The preferred alkoxycarbonyl group is methoxycarbonyl.

The term "substituted phenyl," as used herein, represents a phenyl group substituted with one or two moieties chosen from the group consisting of halogen, hydroxy, cyano, nitro, $C_1$–$C_6$ alkyl, $C_1$–$C_4$ alkoxy, alkoxycarbonyl, protected carboxy, carboxymethyl, hydroxymethyl, amino, protected amino, aminomethyl, or trifluoromethyl. Examples of a substituted phenyl group include 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, 4-hydroxyphenyl, 3-hydroxy-phenyl, 2,4-dihydroxyphenyl, 3-nitrophenyl, 4-nitrophenyl, 4-cyanophenyl, 4-methylphenyl, 4-ethylphenyl, 4-ethoxy-phenyl, 4-carboxyphenyl, 4-(hydroxymethyl)phenyl, 4-aminophenyl, 4-propylphenyl, 4-butylphenyl, 4-t-butyl-phenyl, 3-fluoro-2-methylphenyl, 2,3-difluorophenyl, 2,6-difluorophenyl, 2,6-dimethylphenyl, 2-fluoro-5-methylphenyl, 2,4,6-trifluorophenyl, 2-trifluoromethylphenyl, 2-chloro-5-trifluoromethylphenyl, 2,4-bis(trifluoromethyl)-phenyl, 3,5-bis(trifluoromethyl)phenyl, 2-methoxyphenyl, 3-methoxyphenyl, 3,5-dimethoxyphenyl, 4-hydroxy-3-methyl-phenyl, 3,5-dimethyl-4-hydroxyphenyl, 4-hydroxy-3-(hydroxymethyl)phenyl, 2-amino-5-methylphenyl, 4-amino-3-trifluoromethylphenyl, 3-amino-4-hydroxyphenyl, 2-methyl-4-nitrophenyl, 4-methoxy-2-nitrophenyl, 2,4-dinitrophenyl, 3-cyano-4-nitrophenyl, and the like.

The term "aryl" represents groups such as phenyl, substituted phenyl, and naphthyl. The term "arylalkyl" represents a $C_1$–$C_4$ alkyl group bearing one or more aryl groups. Representatives of this latter group include benzyl, 2-nitrobenzyl, 4-nitrobenzyl, 1-phenylethyl, 2-phenylethyl, 3-phenylpropyl, 4-phenylbutyl, 2-methyl-2-phenylpropyl, (4-chlorophenyl)methyl, (2,6-dichlorophenyl)-methyl, bis (2,6-dichlorophenyl)methyl, (4-hydroxyphenyl)-methyl, (2,4-dinitrophenyl)methyl, triphenylmethyl, (4-methoxyphenyl)diphenylmethyl, bis(4-methoxyphenyl) methyl, ∝naphthyldiphenylmethyl, bis(2-nitrophenyl) methyl, and the like.

The term "affecting" refers to a formula I compound acting as an agonist at an excitatory amino acid receptor. The term "excitatory amino acid receptor" refers to a metabotropic glutamate receptor, a receptor that is coupled to cellular effectors via GTP-binding proteins. The term "cAMP-linked metabotropic glutamate receptor" refers to a metabotropic receptor that is coupled to inhibition of adenylate cyclase activity.

The term "neurological disorder" refers to both acute and chronic neurodegenerative conditions, including cerebral deficits subsequent to cardiac bypass surgery and grafting, cerebral ischemia (for example stroke resulting from cardiac arrest), spinal cord trauma, head trauma, Alzheimer's Disease, Huntington's Chorea, amyotrophic lateral sclerosis, AIDS-induced dementia, perinatal hypoxia, hypoglycemic neuronal damage, ocular damage and retinopathy, cognitive disorders, idiopathic and drug-induced Parkinson's Disease. This term also includes other neurological conditions that are caused by glutamate dysfunction, including muscular spasms, migraine headaches, urinary incontinence, drug tolerance, withdrawal, and cessation (i.e. opiates, benzodiazepines, nicotine, cocaine, or ethanol), smoking cessation, emesis, brain edema, chronic pain, sleep disorders, convulsions, Tourette's syndrome, attention deficit disorder, and tardive dyskinesia.

The term "psychiatric disorder" refers to both acute and chronic psychiatric conditions, including schizophrenia, anxiety and related disorders (e.g. panic attack and stress-related cardiovascular disorders), depression, bipolar disorders, psychosis, and obsessive compulsive disorders.

The present invention includes pharmaceutically-acceptable salts of the formula I compounds. These salts can exist in conjunction with the acidic or basic portion of the molecule and can exist as acid addition, primary, secondary, tertiary, or quaternary ammonium, alkali metal, or alkaline earth metal salts. Generally, the acid addition salts are prepared by the reaction of an acid with a compound of formula I. The alkali metal and alkaline earth metal salts are generally prepared by the reaction of the hydroxide form of the desired metal salt with a compound of formula I, wherein $R^1$ and/or $R^4$ is hydrogen.

Acids commonly employed to form such salts include inorganic acids such as hydrochloric, hydrobromic, hydriodic, sulfuric, and phosphoric acid, as well as organic acids such as para-toluenesulfonic, methanesulfonic, oxalic, para-bromophenylsulfonic, carbonic, succinic, citric, benzoic, and acetic acid, and related inorganic and organic acids. Such pharmaceutically-acceptable salts thus include sulfate, pyrosulfate, bisulfate, sulfite, bisulfite, phosphate, ammonium, monohydrogenphosphate, dihydrogenphosphate, meta-phosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, furmarate, hippurate, maleate, butyne-1, 4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, a-hydroxybutyrate, glycolate, maleate, tartrate, methanesulfonate, propanesulfonate, naphthalene-1-sulfonate, napthalene-2-sulfonate, mandelate, magnesium, tetramethylammonium, potassium, trimethylammonium, sodium, methylammonium, calcium, and the like salts.

The formula I compounds of the present invention possess four asymmetric carbon atoms. The asymmetric centers are the substituted carbon atom bearing the amino and carboxyl groups, the carbon atom where $R^2$ and $R^3$ are attached, and the two ring fusion carbon atoms. The asymmetric carbons are at positions 2, 6, 1, and 5, respectively. Therefore, the compounds of the present invention can exist as essentially pure optical isomers, a mixture of two enantiomers (including racemic modifications), and a mixture of two diastereomers. When $R^2$ is $CO_2R^4$, and $R^1$, $R^3$, and $R^4$ are hydrogen, the biologically active and most preferred stereoisomer, as determined by receptor binding assays, has a positive optical rotation ($\alpha_D$). The X-ray single crystal structure of this most preferred enantiomer was solved, providing the relative stereochemical configuration as shown below:

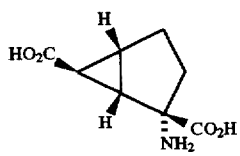

The absolute stereochemical configuration of this most preferred enantiomer has been determined to be 1S, 2S, 5R, 6S. The present invention, therefore, includes the stereoisomeric Formula I compounds having this same preferred stereochemical configuration, mixtures of enantiomers containing this preferred stereochemical configuration (including racemates), and mixtures of diastereomers containing this preferred stereochemical configuration.

While all the formula I compounds of the present invention are believed to selectively affect the negatively-coupled cAMP-linked metabotropic glutamate receptors, certain compounds of the invention are preferred for such use. Preferably, $R^2$ is $CO_2R^4$, $R^3$ is hydrogen, and $R^1$ and $R^4$ are independently hydrogen, $C_1$–$C_6$ alkyl, aryl, or arylalkyl. Representative compounds from this preferred group of formula I compounds include 2-aminobicyclo[3.1.0]hexane-2,6-dicarboxylic acid, dimethyl 2-aminobicyclo[3.1.0] hexane-2,6-dicarboxylate, diethyl 2-aminobicyclo[3.1.0] hexane-2,6-dicarboxylate, dibutyl 2-aminobicyclo[3.1.0] hexane-2,6-dicarboxylate, dihexyl 2-aminobicyclo[3.1.0] hexane-2,6-dicarboxylate, diphenyl 2-aminobicyclo[3.1.0] hexane-2,6-dicarboxylate dibenzyl 2-aminobicyclo[3.1.0] hexane-2,6-dicarboxylate. Certain compounds of the present invention are more preferred for use in affecting the cAMP-linked metabotropic glutamate receptors. More preferably, $R^1$ and $R^4$ are independently hydrogen, $C_1$–$C_4$ alkyl, aryl, or arylalkyl. Representative compounds from this more preferred group of compounds include 2-aminobicyclo-[3.1.0] hexane-2,6-dicarboxylic acid, dimethyl 2-aminobicyclo [3.1.0]hexane-2,6-dicarboxylate, diethyl 2-aminobicyclo [3.1.0]hexane-2,6-dicarboxylate, dibutyl 2-aminobicyclo [3.1.0]hexane-2,6-dicarboxylate, diphenyl 2-aminobicyclo [3.1.0]hexane-2,6-dicarboxylate and dibenzyl 2-aminobicyclo[3.1.0]hexane-2,6-dicarboxylate.

Most preferably, the compound of formula (I) is (+)-2-aminobicyclo[3.1.0]hexane-2,6-dicarboxylic acid, a $C_1$–$C_4$ alkyl, aralkyl or aryl ester thereof or a pharmaceutically acceptable salt thereof.

Certain compounds are most preferred for use in affecting the cAMP-linked metabotropic glutamate receptors. Most preferably $R^1$ and $R^4$ are independently hydrogen or $C_1$–$C_4$ alkyl. Representative compounds from this group of most preferred compounds include 2-aminobicyclo[3.1.0]hexane-2,6-dicarboxylic acid, dimethyl 2-aminobicyclo[3.1.0] hexane-2,6-dicarboxylate, diethyl 2-aminobicyclo[3.1.0] hexane-2,6-dicarboxylate, dibutyl 2-aminobicyclo[3.1.0] hexane-2,6-dicarboxylate, and dipropyl 2-aminobicyclo [3.1.0]hexane-2,6-dicarboxylate.

While all the formula X compounds of the present invention are believed to be useful for the synthesis of the formula I compounds, certain compounds are preferred. Preferably, $R^{2a}$ is $CO_2R^{4a}$ and $R^{3a}$ is hydrogen. More preferably; $R^{4a}$ is hydrogen or a $C_1$–$C_6$ alkyl group, for example an ethyl group.

The formula I compounds of the present invention are generally synthesized by cyclopropanation of a 2-cycloalken-1-one, formula II compound wherein X is as defined above for the formula I compounds. The formula I compounds wherein $R^3$ is hydrogen and $R^2$ is $CO_2R^4$ are prepared as shown in Scheme I.

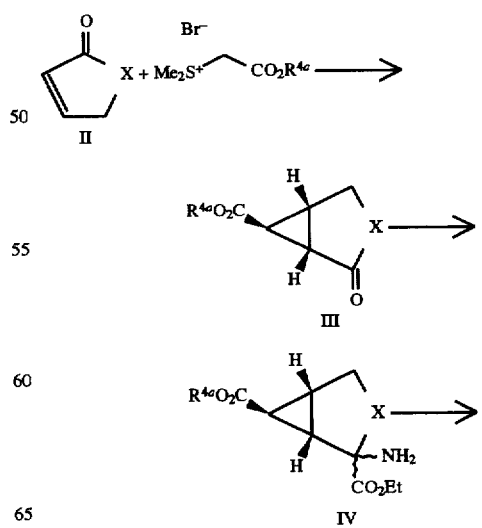

-continued
Scheme I

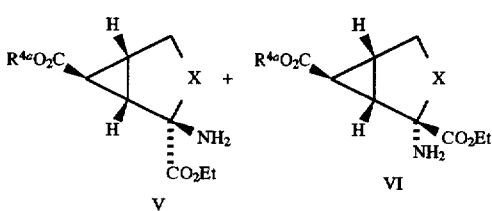

Generally, the formula II compound is reacted with (protected carboxy)methyl dimethylsulfonium bromide to produce bicyclic compound of formula III wherein $R^{4a}$ is a carboxy protecting group. This compound is converted to an amino acid by a Strecker or a Bucherer-Bergs reaction followed by hydrolysis, and esterified to produce the formula IV compounds as a mixture of isomers. This isomeric mixture is separated to produce the formula V and formula VI compounds. These compounds are then hydrolyzed to produce the formula I compounds wherein $R^2$ is $CO_2R^4$, and $R^1$ and $R^4$ are hydrogen.

More specifically, a 2-cycloalken-1-one is reacted with (protected carboxy)methyl dimethylsulfonium bromide to produce bicyclic intermediate III. This cyclopropanation is conveniently carried in an organic solvent in the presence of an amine base. Suitable solvents for this reaction include acetonitrile, dichloromethane, benzene, toluene, and xylene; preferably acetonitrile or dichloromethane. Amine bases suitable for use in this reaction are non-nucleophilic bases such as 1,8-diazabicyclo[5.4.0] undec-7-ene, pyridine, and collidine. The preferred amine base for use in this reaction is 1,8-diazabicyclo[5.4.0]undec-7-ene. Preferably, the carboethoxymethyl dimethylsulfonium bromide is reacted with the amine base, producing ethyl (dimethylsulfuranylidene) acetate in situ. The resulting mixture is treated with a 2-cycloalken-1-one. Examples 2-cycloaken-1-ones include 2-cyclopenten-1-one, 2-cyclohexen-1-one, 2-cyclohepten-1-one, and 2-cycloocten-1-one. The reaction is generally carried out at a temperature of about 25° C. to about 50° C., preferably at a temperature of about 25° C. to about 30° C. The reaction is generally complete after about 18 hours to about three days.

Bicyclic intermediate III is converted to a bicyclic amino acid by a Strecker or a Bucherer-Bergs reaction followed by hydrolysis of the intermediates. Krauch and Kunz, Organic Name Reactions, 76, (1964) (see references contained therein). Preferably bicyclic ketone III is reacted with an aqueous solution of potassium cyanide or sodium cyanide and ammonium carbonate to produce hydantoin intermediates. This reaction is typically carried out in alcoholic solvent, such as ethanol or methanol. The reaction is typically carried out at a temperature of about 25° C. to about the reflux temperature of the solvent, preferably at about 50° C. The reaction is generally complete after a period of about 18 hours. The isomeric hydantoins may be isolated and purified as described below. Preferably, the mixture of isomeric hydantoins is hydrolyzed using sodium hydroxide and subsequently esterified, without isolation or purification, to a formula V or formula VI compound. This hydrolysis is typically carried out at the reflux temperature of the solvent for about 15 hours to about 20 hours.

The products of the hydrolysis, a mixture of isomeric formula I compounds wherein $R^1$ is hydrogen, are preferably esterified prior to separation of the diastereomers and enantiomers. When the carboxy protecting group is removed during the hydrolysis, a diester is subsequently prepared. A solution of the carboxylic acid or dicarboxylic acid in an alcohol, such as methanol, ethanol, i-propanol, or n-butanol, is treated with thionyl chloride and heated to reflux. Typically, a solution of the hydrolysis product is cooled to about 0° C. before addition of the thionyl chloride. The esterification is generally complete after about 48 hours.

The diastereomeric products, formula V and formula VI compounds, are separated using standard techniques. The preferred methods for separation are crystallization and/or chromatography. The formula V and VI compounds may be selectively crystallized by formation of an acid addition salt, such as the oxalate salt. This salt is prepared by treating an ethyl acetate solution, containing a mixture of the formula V and VI compounds, with oxalic acid and ethanol. Additional ethanol may be added to aid in crystallization of one of the diastereomers. This procedure gives a crystalline material enriched in one isomer, and a filtrate (mother liquor) enriched in the other isomer. The compounds may be further purified using chromatography, such as silica-gel chromatography.

The formula V and VI compounds are hydrolyzed, if necessary, and the carboxy protecting group removed to prepare the formula I compounds wherein $R^1$ and $R^4$ are hydrogen. The compounds are typically hydrolyzed by treating a solution of the formula V or formula VI compound in an organic solvent, such as tetrahydrofuran, with aqueous base, such as sodium hydroxide. This hydrolysis is typically carried out at room temperature, and requires about 18 hours for completion. The carboxy protecting groups are removed using standard synthetic methods. See McOmie and Greene and Wuts.

The enantiomers of each diastereomeric pair of intermediate V and VI compounds are resolved using standard resolution techniques. See Jacques, Collet, and Wilen, Enantiomers, Racemates, and Resolutions, (1981). The preferred method for resolution of the enantiomers is the formation of diastereomeric salts between the racemic modifications and optically active (chiral) resolving agents. Jacques, Collet, and Wilen Chapter 5. The formula V and VI compounds in which $R^{4a}$ represents a carboxy protecting group can be resolved using acidic chiral resolving agents. Examples of suitable acidic chiral resolving agents include (+)-camphoric acid, (+) and (−)-dibenzoyltartaric acid, diacetoneketogulonic acid, lasalocid, (+) and (−)-mandelic acid, (+) and (−)-malic acid, (+) and (−)-quinic acid, (+) and (−)-tartaric acid, (+)-di-p-toluoyl-D-tartaric acid, and (−)-di-p-toluoyl-L-tartaric acid. The preferred acidic resolving agents for resolution of the formula V and VI compounds in which $R^{4a}$ represents a carboxy protecting group are (+)-di-p-toluoyl-D-tartaric acid, and (−)-di-p-toluoyl-L-tartaric acid. The formula V and VI compounds in which $R^{4a}$ represents hydrogen can be resolved using basic chiral resolving agents. An example of a basic chiral resolving agent is (S)-1-phenylethylamine.

Alternatively, the bicyclic formula III compound can be converted to a mixture of diastereomeric hydantoins as shown in Scheme II.

Scheme II

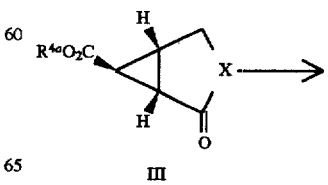

III

-continued
Scheme II

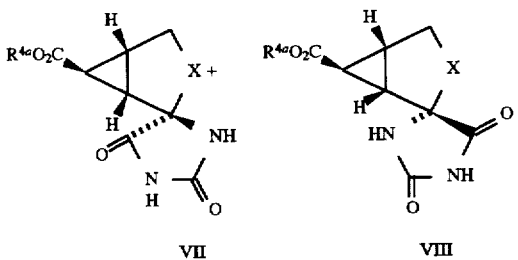

Bicyclic intermediate III, prepared as described above, is reacted with a solution of potassium cyanide or sodium cyanide and ammonium carbonate to produce diastereomeric hydantoin intermediates, formula VII and formula VIII compounds. This reaction is typically carried out in a mixture of water and an alcohol, such as methanol or ethanol. The reaction is carried out at a temperature of about 55° C. to about 60° C., and is generally complete after about 18 hours to about 4 days. The diastereomeric products are separated using standard techniques, such as crystallization and/or chromatography. Preferably, the formula VII and VIII compounds are separated by crystallization.

The formula VII and VIII compounds in which $R^{4a}$ represents hydrogen may be resolved using a basic chiral resolving agent. An example of a basic chiral resolving agent is (R)-1-phenylethylamine.

The hydantoin intermediate, the formula VII or VIII compound, is converted to a formula I compound, wherein $R^1$ and $R^4$ are hydrogen, by hydrolysis. The hydantoin group and the ester group are hydrolyzed using aqueous base, such as sodium hydroxide, or aqueous acid, such as hydrochloric acid. This hydrolysis is typically carried out at a temperature of about 100° C. to about 150° C. The resulting formula I compound is purified using ion-exchange chromatography.

The formula I compounds wherein $R^2$ is hydrogen and $R^3$ is $CO_2R^{4a}$, are prepared as shown in Scheme III.

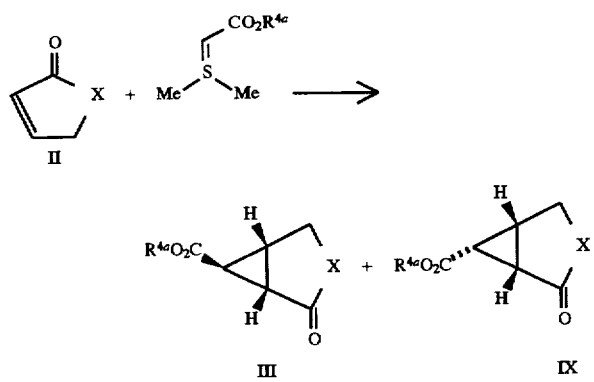

A 2-cycloalken-1-one is reacted with a carboxy protected (dimethylsulfuranylidene) acetate to produce isomeric bicyclic intermediates III and IV. This cyclopropanation is carried out in an organic solvent at a temperature of about 45° C. to about 85° C. Suitable solvents include benzene, toluene, xylene, and acetonitrile. Preferably, the reaction is carried out in benzene at 50° C. The diastereomeric products are separated using silica gel chromatography. The formula IX compound is converted to the formula I compounds using the procedures described above for conversion of the formula III compounds.

The compounds of formula III in which X represents $CH_2$ may also be prepared as shown in Scheme IV.

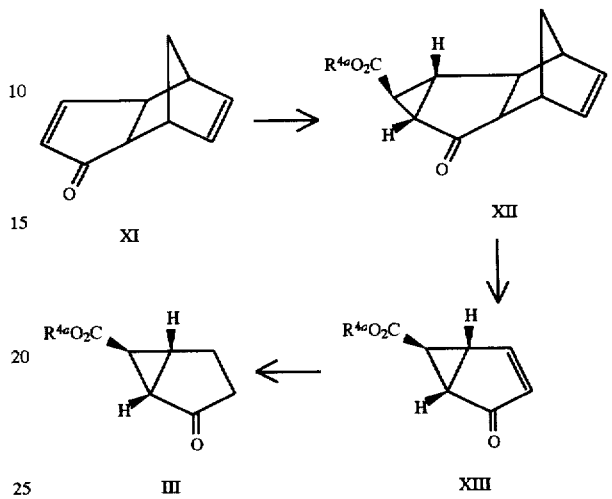

A compound of formula XI is reacted with a (protected carboxy)methyl dimethylsulfonium bromide to produce a compound of formula XII in which $R^{4a}$ is a carboxy protecting group. The reaction is conveniently performed according to a method analogous to that described herein for the cyclopropanation of a compound of formula II. The resultant compound of formula XII is then converted into a compound of formula XIII by heating, for example at a temperature in the range of from 160° to 500° C., preferably from 180° to 300° C. Heating the compound of formula XII liberates cyclopentadiene. The procedure is conveniently performed under an inert gas, such as nitrogen, and in the presence of an inert organic solvent, such as dichlorobenzene. The resultant compound of formula XIII is then converted into a compound of formula III by reduction, for example, by hydrogenation in the presence of palladium on charcoal. The reduction is conveniently performed at a temperature in the range of from 0° to 50° C. Suitable solvents for the reduction include alcohols, such as ethanol, ester such as ethyl acetate, aromatic hydrocarbons such as toluene and amides such as dimethylformanide.

It will be appreciated that by using an optically active compound of formula XI as starting material, an optically active compound of formula III may be obtained.

The compounds of formula XIII are believed to be novel, and are provided as a further aspect of the invention.

The compound of formula XI (including the optically active forms) may be prepared according to the method described in Klunder et al., Tetrahedron Lett., 1986, 27, 2543 and Takano et al, Synlett 1991, 636.

The formula I compounds wherein $R^1$ and $R^4$ are $C_1$-$C_{10}$ alkyl, $C_2$-$C_{10}$ alkenyl, aryl, or arylalkyl, are prepared from the corresponding compounds wherein $R^1$ and $R^4$ are hydrogen. These compounds are generally prepared using standard synthetic methodologies. In a typical example, the formula I compound, wherein $R^1$ and $R^4$ are hydrogen, can be reacted with a $C_1$-$C_{10}$ alkyl, $C_2$-$C_{10}$ alkenyl, aryl, or arylalkyl alcohol in the presence of an acid to produce the corresponding ester. Typically, this reaction is carried out with an excess of the alcohol in the presence of a catalytic amount of concentrated sulfuric acid.

The formula I compounds wherein $R^1$ and $R^4$ are not identical may be prepared from the diacid, $R^1$ and $R^4$ are hydrogen, using standard synthetic organic techniques. For example, the chemistry that has been developed for selective functionalization of the carboxyl groups of glutamic and aspartic acids is applicable. Alternatively, by choosing a carboxy protecting group on the formula X compound that is stable under the hydrolysis condition for the hydantoin group, the carboxyl groups may be selectively manipulated.

The formula I compounds of the present invention are agonists of certain metabotropic excitatory amino acid receptors. Specifically, the formula I compounds are agonists of the negatively-coupled cAMP-linked metabotropic glutamate receptors. Therefore, another aspect of the present invention is a method of affecting an excitatory amino acid receptor in mammals, which comprises administering to a mammal requiring modulated excitatory amino acid neurotransmission a pharmaceutically-effective amount of a compound of formula I. The term "pharmaceutically-effective amount" is used to represent an amount of the compound of the invention which is capable of affecting the excitatory amino acid receptors. By affecting, a compound of the invention is acting as an agonist. When a compound of the invention acts as an agonist, the interaction of the compound with the EAA receptor mimics the response of the interaction of this receptor with its natural ligand (i.e. L-glutamate).

The particular dose of compound administered according to this invention will of course be determined by the particular circumstances surrounding the case, including the compound administered, the route of administration, the particular condition being treated, and similar considerations. The compounds can be administered by a variety of routes including oral, rectal, transdermal, subcutaneous, intravenous, intramuscular, or intranasal routes. Alternatively, the compound may be administered by continuous infusion. A typical daily dose will contain from about 0.001 mg/kg to about 100 mg/kg of the active compound of this invention. Preferably, daily doses will be about 0.05 mg/kg to about 50 mg/kg, more preferably from about 0.1 mg/kg to about 20 mg/kg.

A variety of physiological functions have been shown to be subject to influence by excessive or inappropriate stimulation of excitatory amino acid transmission. The formula I compounds of the present invention are believed to have the ability to treat a variety of neurological disorders in mammals associated with this condition, including acute neurological disorders such as cerebral deficits subsequent to cardiac bypass surgery and grafting, cerebral ischemia (e.g. stroke and cardiac arrest), spinal cord trauma, head trauma, perinatal hypoxia, and hypoglycemic neuronal damage. The formula I compounds are believed to have the ability to treat a variety of chronic neurological disorders, such as Alzheimer's disease, Hungington's Chorea, amyotrophic lateral sclerosis, AIDS-induced dementia, ocular damage and retinopathy, cognitive disorders, and idopathic and drug-induced Parkinson's. The present invention also provides methods for treating these disorders which comprises administering to a patient in need thereof an effective amount of a compound of formula I.

The formula I compounds of the present invention are also believed to have the ability to treat a variety of other neurological disorders in mammals that are associated with glutamate dysfunction, including muscular spasms; convulsions; migraine headaches; urinary incontinence; psychosis; drug tolerance, withdrawal, and cessation (i.e. opiates, benzodiazepines, nicotine, cocaine, or ethanol); smoking cessation; anxiety and related disorders (e.g. panic attack and stress-related disorders); emesis; brain edema; chronic pain; sleep disorders; Tourette's syndrome; attention deficit disorder; and tardive dyskinesia. Therefore, the present invention also provides methods for treating these disorders which comprise administering to a patient in need thereof an effective amount of the compound of formula I.

The compounds of the present invention are agonists of cAMP-linked metabotropic glutamate receptors. These compounds are negatively coupled through the receptor to adenyl cyclase, inhibiting the formation of cyclic adenosine monophosphate. The formula I compounds of the present invention are, therefore, believed to have the ability to treat a variety of psychiatric disorders, such as schizophrenia, anxiety and related disorders (e.g. panic attack and stress-related disorders), depression, bipolar disorders, psychosis, and obsessive compulsive disorders. The present invention also provides methods for treating these disorders which comprises administering to a patient in need thereof an effective amount of a compound of formula I.

Experiments were performed to demonstrate the ability of the formula I compounds to affect the excitatory amino acid receptors. The affinity of the compounds for metabotropic glutamate receptors was demonstrated by the selective displacement of (1S,3R)-1-aminocyclopentane-1,3-dicarboxylic acid-sensitive [$^3$H]glutamate binding to rat brain cell membranes. The binding of [$^3$H]glutamate ([$^3$H] Glu) was conducted with crude membranes of rat forebrain as described by Schoepp and True, Schoepp and True, *Neuroscience Lett.*, 145, 100–104 (1992); Wright, McDonald, and Schoepp, *J. Neurochem.*, 63, 938–945 (1994). The concentration of the formula I compound that inhibited 50% binding ($IC_{50}$), or the percent displacement of [$^3$H]Glu at a 10 μM or 100 μM concentration of the formula I compound, is shown in Table I.

TABLE I

| Receptor Binding of Formula I Compounds | |
|---|---|
| Compound[a] no. | $IC_{50}$ (μM) |
| 3[b] | 0.32 |
| 6[c] | 0.18 |
| 7[c] | 160.78 |
| 8[b] | 3.2 |

[a]Compound numbers are from experimental section
[b]Compound tested as a mixture of enantiomers
[c]Compound tested as pure enantiomer
[d]Compound tested as a mixture of diastereomers Compounds 3, 6, 7 and 8 are all dicarboxylic acids. In general, it has been found that the ester derivatives (those compounds of formula I in which one or both of $R^1$ and $R^4$ are not hydrogen) are inactive in the receptor binding test. However, it is believed that these compounds are hydrolysable in vivo to the corresponding acid and can therefore function as pro-drugs. It will be appreciated that the present invention provides the active dicarboxylic acids as well as any pro-drug forms that are capable of generating the active acid in vivo.

The formula I compounds are effective in affecting the cAMP-linked metabotropic glutamate receptors. Representative compounds were tested for their ability to decrease forskolin-stimulated cAMP formation in the rat hippocampus and the rat cerebral cortex, using the procedures described in Schoepp and Johnson, Schoepp and Johnson, Neurochem. Int., 22, 277–283 (1993). The results of these experiments are shown in Table II.

TABLE II

| | Inhibition of Forskolin-Stimulated cAMP Formation | |
|---|---|---|
| | $EC_{50}$ (µM) | |
| Compound no. | 6 | 7 |
| Rat cerebral cortex | .055 ± .017 | 22.0 ± 3.4 |
| Rat hippocampus | .036 ± .015 | 29.4 ± 3.04 |

The ability of formula I compounds to treat anxiety or a related disorder may be demonstrated using the well known fear potentiated startle and elevated plus maze models of anxiety described respectively in Davis, *Psychopharmacology*, 62:1;1979 and Lister, *Psychopharmacol*, 92:180–185; 1987

In the fear potentiated startle model, animals are exposed to a neutral stimulus such as light (conditioned stimulus) with an aversive stimulus such as a shock (unconditioned stimulus). Following conditioning, when the animals are presented with a loud acoustic stimulus, larger startle responses are elicited when the startle stimulus is preceded by light.

The elevated plus maze model is based upon the natural aversion of rodents to height and open spaces.

Diazepam and buspirone hydrochloride, which are clinically proven anxiolytics, are effective at reducing the fear (increased startle response) associated with the presentation of light in the fear potentiated startle model, and in reducing the fear of open spaces in the elevated plus maze model.

Male Long Evans rats (180–400 g) or male NIH Swiss mice (18–35 g) were obtained from Harlan Sprague-Dawley, Cumberland, Ind., USA and acclimated at least 3 days before testing. Animals were housed at 23±2° C.(relative humidity 30% to 70%) and given Purina Certified Rodent Chow and water ad libitum. The photoperiod was 12 hours of light and 12 hours of dark, with dark onset at approximately 1800 hours.

Test compounds were dissolved in a vehicle of purified water and neutralized with 5N NaOH to a pH of 7–8 when applicable. Diazepam (Sigma Chemical Company, St. Louis, Mo.) was suspended in purified water by the dropwise addition of Tween 80. Control animals received the respective vehicle.

Fear Potentiated Startle

SL-LAB (San Diego Instruments, San Diego, Calif.) chambers were used for conditioning sessions and for the production and recording of startle responses. A classical conditioning procedure was used to produce potentiation of startle responses. Briefly, on the first 2 days, rats were placed into dark startle chambers in which shock grids were installed. Following a 5-minute acclimation period, each rat received a 1 mA electric shock (500 ms) preceded by a 5 second presentation of light (15 watt) which remained on for the duration of the shock. Ten presentations of the light and shock were given in each conditioning session, rats were gavaged with a solution of test compound of water and startle testing sessions were conducted. A block of 10 consecutive presentations of acoustic startle stimuli (110 dB, non-light-paired) were presented at the beginning of the session in order to minimize the influences of the initial rapid phase of habituation to the stimulus. This was followed by 20 alternating trials of the noise alone or noise preceded by the light. Excluding the initial trial block, startle response amplitudes for each trial type (noise-alone vs. light+noise) were averaged for each rat across the entire test session. Data are presented as the difference between noise-alone and light+noise. The result are shown in Table III.

TABLE III

| Fear Potential Startle | |
|---|---|
| Test Compound | $ED_{50}$ (mg/kg, p.o.) |
| Compound 6 | 0.3 |
| Compound 7 | Inactive* |
| Diazepam | 0.4 |

*at highest dose tested, 10 mg/kg p.o.

Automated Elevated Plus Maze

Construction of the elevated plus-maze was based on a design validated for mice by Lister (1987). The entire maze was made of clear Plexiglas. The maze was comprised of two open arms (30×5×0.25 cm) and two enclosed arms (30×5×15 cm). The floor of each maze arm was corrugated to provide texture. The arms extended from a central platform and angled at 90 degrees from each other. The maze was elevated to a height of 45 cm above the floor and illuminated by red light. Individual infrared photocells were mounted along each arm of the maze to monitor closed, open, or nosepoke activity. Mice were individually placed on the central platform of the maze and the number of closed arm, open arm, and nosepoke (poking head only into open arm from closed arm of maze) counts were recorded and used as a measure of arm entries and time spent on various sections of the maze over a five-minute test period.

Oral administration of compound 6 produced significant increases in open arm activity at doses of 1, 3 and 10 mg/kg. Nosepoke counts showed a significant increase at 3 mg/kg. Closed arm activity counts were not significantly altered at any dose of compound 6.

The ability of formula I compounds to protect a warm blooded mammal from the effects of drug withdrawal or cessation may be demonstrated using an auditory startle model. In this model, animals are dosed with a drug (nicotine or diazepam), then dosing is discontinued. This cessation of drug dosing elicits an increased startle response to auditory stimuli. Test compounds are then administered to animals to determine whether they are capable of attenuating the increased startle response.

Long Evans rats (200–400 g; Harlan Sprague Dawley, Columbus, Ind.) were individually housed in a controlled environment on a 12 hour light-dark cycle and given free access to food (Purina Rodent Chow) and water. Rats were anesthetized with isoflurane and Alzet osmotic pumps (Alza Corporation) were implanted subcutaneously.

Test compound was dissolved in a vehicle of purified water and neutralized with 5N NaOH to a PH of 7–8 when applicable. Diazepam (Sigma Chemical Company, St. Louis, Mo.) was suspended in a vehicle consisting of 40% PEG 300, 10% EtOH, 2% benzyl alcohol, 1% Tween 80, and 47% purified water. Nicotine (Research Biochemicals Inc., Natick, Mass.) was dissolved in saline. Control animals received the respective vehicle.

Nicotine withdrawal

Pumps were filled to deliver nicotine (6 mg/kg/day, s.c.), diazepam (10 mg/kg/day, s.c.), test compound (0,1,3,10 mg/kg, s.c.) or vehicle. Twelve days following subcutaneous implantation of pumps, rats were anesthetized with isoflurane and the pumps were removed. During withdrawal (following pump removal), the auditory startle response (peak amplitude, Vmax) of individual rats was recorded using San Diego Instruments startle chambers (San Diego, Calif.). Startle sessions consisted of a 5-minute adaptation period at a background noise level of 70±2 dBA immediately followed by 25 presentations of auditory stimuli (120±2 dBA noise, 50 ms duration) presented at 8-second intervals. Peak startle amplitudes were then averaged for all 25 presentations of stimuli for each session and all data are presented here as overall session means. Auditory startle responding was evaluated daily on withdrawal days 1,2,3,4 or 5. Baseline startle responding was evaluated prior to pump removal on day 12.

Auditory startle responding was significantly increased through the first three days following cessation of chronic nicotine exposure when compared to control rats receiving water. Rats given a replacement dose of nicotine at doses of 0.03 mg/kg, i.p., or higher did not display the same heightened startle response seen for animals with no nicotine replacement. Pretreatment with compound 6 produced a dose-dependent blockade of the withdrawal-induced increase in startle responding as well. A significant attenuation of the heightened startle was apparent at 3 mg/kg, p.o., dose of compound 6 when compared to nicotine controls ($ED_{50}$=0.7 mg/kg, i.p.).

Diazepam Withdrawal

Auditory startle responding was significantly increased through the first four days following cessation of chronic diazepam exposure when compared to control rats receiving vehicle. Replacement doses of 3 and 10 mg/kg, i.p., diazepam did not block the increased startle responding and in some instances further increased reactivity indicating tolerance. Rats which received 30 mg/kg, i.p. diazepam replacement daily 60 minutes before evaluation of startle responding, did not show increased reactivity following diazepam cessation on days 1 through 4 when compared to the diazepam control. Pretreatment with Compound 6 blocked the expected increase in startle responding which followed cessation of diazepam exposure. Doses of 0.1 and 0.3 mg/kg, p.o. of compound 6 significantly attenuated enhanced startle when compared to control responding ($ED_{50}$=0.1 mg/kg, p.o.).

The compounds of the present invention are preferably formulated prior to administration. Therefore, another aspect of the present invention is a pharmaceutical formulation comprising a compound of formula I in combination with one or more pharmaceutically-acceptable carriers, diluents, or excipients. The present pharmaceutical formulations are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, dermal patch, subcutaneous implant, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, stearic acid, and mineral oil. The formulations can additionally include lubricating agents, wetting agents (surfactants), emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 1 mg to about 500 mg, more preferably about 5 mg to about 200 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1

Hard gelatin capsules are prepared using the following ingredients:

| | Quantity (mg/capsule) |
|---|---|
| 2-Aminobicyclo[3.1.0]hexane-2,6-dicarboxylic Acid | 250 |
| Starch, dried | 200 |
| Magnesium stearate | 10 |
| Total | 460 mg |

The above ingredients are mixed and filled into hard gelatin capsules in 460 mg quantities.

Formulation 2

A tablet is prepared using the ingredients below:

| | Quantity (mg/tablet) |
|---|---|
| 2-Aminobicyclo[3.1.0]hexane-2,6-dicarboxylic Acid | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

| | Weight % |
|---|---|
| 2-Aminobicyclo[3.1.0]hexane-2,6-dicarboxylic Acid | 0.25 |
| Ethanol | 29.75 |
| Propellant 22 | 70.00 |
| (chlorodifluoromethane) | |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made as follows:

| | |
|---|---|
| 2-Aminobicyclo[3.1.0]hexane-2,6-dicarboxylic Acid | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5

Capsules each containing 80 mg of active ingredient are made as follows:

| | |
|---|---|
| 2-Aminobicyclo[3.1.0]hexane-2,6-dicarboxylic Acid | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6

Suppositories each containing 225 mg of active ingredient may be made as follows:

| | |
|---|---|
| 2-Aminobicyclo[3.1.0]hexane-2,6-dicarboxylic Acid | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of active ingredient per 5 ml dose are made as follows:

| | |
|---|---|
| 2-Aminobicyclo[3.1.0]hexane-2,6-dicarboxylic Acid | 50 mg |

Formulation 7
*—continued*

Suspensions each containing 50 mg of active ingredient per 5 ml dose are made as follows:

| | |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation may be prepared as follows:

| | |
|---|---|
| 2-Aminobicyclo[3.1.0]hexane-2,6-dicarboxylic Acid | 100 mg |
| Mannitol | 100 mg |
| 5 N Sodium hydroxide | 200 μl |
| Purified water to total | 5 ml |

The following Examples further illustrate the compounds of the present invention and the methods for their synthesis. The Examples are not intended to be limiting to the scope of the invention in any respect, and should not be so construed. All experiments were run under a positive pressure of dry nitrogen or argon. All solvents and reagents were purchased from commercial sources and used as received, unless otherwise indicated. Dry tetrahydrofuran (THF) was obtained by distillation from sodium or sodium benzophenone ketyl prior to use. Proton nuclear magnetic resonance ($^1$H NMR) spectra were obtained on a GE QE-300 spectrometer at 300.15 MHz, a Bruker AM-500 spectrometer at 500 MHz, or a Bruker AC-200P spectrometer at 200 MHz. Free atom bombardment mass spectroscopy (FABMS) was performed on a VG ZAB-2SE instrument. Field desorption mass spectroscopy (FDMS) was performed using either a VG 70SE or a Varian MAT 731 instrument. Optical rotations were measured with a Perkin-Elmer 241 polarimeter. Chromatographic separation on a Waters Prep 500 LC was generally carried out using a linear gradient of the solvents indicated in the text. The reactions were generally monitored for completion using thin layer chromatography (TLC). Thin layer chromatography was performed using E. Merck Kieselgel 60 $F_{254}$ plates, 5 cm×10 cm, 0.25 mm thickness. Spots were detected using a combination of UV and chemical detection (plates dipped in a ceric ammonium molybdate solution [75 g of ammonium molybdate and 4 g of cerium (IV) sulfate in 500 mL of 10% aqueous sulfuric acid] and then heated on a hot plate). Flash chromatography was performed as described by Still, et al. Still, Kahn, and Mitra, *J. Org. Chem.*, 43, 2923 (1978). Elemental analyses for carbon, hydrogen, and nitrogen were determined on a Control Equipment Corporation 440 Elemental Analyzer, or were performed by the Universidad Complutense Analytical Centre (Facultad de Farmacia, Madrid, Spain). Melting points were determined in open glass capillaries on a Gallenkamp hot air bath melting point apparatus or a Büchi melting point apparatus, and are uncorrected. The number in parenthesis after the compound name refers to the compound number.

Preparation 1

Carboethoxymethyl Dimethylsulfonium Bromide

A solution of ethyl bromoacetate (265 g) and dimethyl sulfide (114 g) in acetone (500 mL) was stirred at room temperature. After three days, the title compound was isolated by filtration of the reaction mixture. Melting point 88°–90° C.

EXAMPLE 1

(1SR,5RS,6SR) Ethyl 2-Oxobicyclo[3.1.0]hexane-6-carboxylate

A suspension of carboethoxymethyl dimethylsulfonium bromide (45.5 g) in toluene (350 mL) was treated with 1,8-diazabicyclo[5.4.0]undec-7-ene (30.2 g). The resulting mixture was stirred at room temperature. After one hour, the reaction mixture was treated with 2-cyclopenten-1-one (19.57 g). After an additional 18 hours, the reaction mixture was added to a 1N hydrochloric acid/sodium chloride solution. The resulting mixture was extracted with diethyl ether. The combined ether extracts were dried over magnesium sulfate, filtered, and concentrated in vacuo. The residue was purified using silica-gel chromatography, eluting with a linear gradient of 10% ethyl acetate/hexanes to 50% ethyl acetate/hexanes, to give 22.81 g of the title compound. Melting point: 36°–38° C.

FDMS: m/z=168 (M+)

Analysis calculated for $C_9H_{12}O_3$: C, 64.27; H, 7.19. Found: C, 64.54; H, 7.11.

EXAMPLE 2

(1SR,2RS, 5RS,6SR) Diethyl 2-Aminobicyclo[3.1.0]-hexane-2,6-dicarboxylate (1) and (1SR,2SR, 5RS,6SR) Diethyl 2-Aminobicyclo[3.1.0]-hexane-2,6-dicarboxylate (2)

A solution of the compound prepared as described in Example 1 (22.81 g) in ethanol (200 mL) was treated with an aqueous solution of potassium cyanide (9.71 g) and ammonium carbonate (21.2 g) in water (200 mL). The resulting mixture was heated to about 50° C. After about 18 hours, the reaction mixture was allowed to cool to room temperature and treated with sodium hydroxide (16.2 g). The resulting mixture was heated to reflux. After about 18 hours, the reaction mixture was allowed to cool to room temperature, then cooled to 0° C. The pH of the cold mixture was adjusted to pH 1 by the addition of concentrated hydrochloric acid. This mixture was concentrated to dryness in vacuo. The residue was dissolved in ethanol, cooled to 0° C., and treated with thionyl chloride (80.6 g). The resulting mixture was heated to reflux. After about 48 hours, the reaction was concentrated to dryness in vacuo. The residue was treated with 1N sodium hydroxide, and the resulting mixture extracted with diethyl ether. The combined ether extracts were dried over potassium carbonate, filtered, and concentrated in vacuo to give 24.6 g of a mixture of the title compounds.

EXAMPLE 3

(1SR,2SR,5RS,6SR) Diethyl 2-Aminobicyclo[3.1.0]-hexane-2,6-dicarboxylate (2)

A solution of the compounds prepared as described in Example 2 (20.71 g) in ethyl acetate (200 mL) was treated with a solution of oxalic acid (15.46 g) in ethanol (50 mL). The resulting mixture was stirred at room temperature. After one hour, the reaction mixture was treated with additional ethanol (50 mL). After 18 hours, the mixture was filtered, and the filtrate was evaporated to dryness in vacuo. The residue was treated with 1N sodium hydroxide, and the resulting mixture extracted with diethyl ether. The combined ether extracts were washed with brine, dried over potassium carbonate, filtered, and concentrated in vacuo. The residue was purified by silica-gel chromatography, eluting with methylene chloride:5% ammonium hydroxide/methanol (97:3), to give 15.41 g of the title compound.

FDMS: m/z=242 (M+H).

Analysis calculated for $C_{12}H_{19}NO_4$: C, 59.74; H, 7.94; N, 5.81. Found: C, 59.78; H, 8.13; N, 5.77.

EXAMPLE 4

(1SR,2SR,5RS,6SR) 2-Aminobicyclo[3.1.0]hexane-2,6-dicarboxylic Acid (3)

A solution of the compound prepared as described in Example 3 (3.1 g) in 2N sodium hydroxide (25 mL) and tetrahydrofuran (25 mL) was stirred at room temperature. After about 18 hours, the tetrahydrofuran was removed under reduced pressure, and the pH of the resulting solution was adjusted to pH 9. The title compound was purified using ion-exchange chromatography (Bio-Rad AG1-X8), eluting with 50% acetic acid/water, to give 2.12 g. Melting point: >250° C. (dec).

FDMS: m/z=186 (M+H).

Analysis calculated for $C_8H_{11}NO_4$: C, 51.89; H, 5.99; N, 7.56. Found: C, 51.74; H, 6.15; N, 7.45.

EXAMPLE 5

(1SR,2SR,5RS,6SR) Diethyl 2-Aminobicyclo[3.1.0]hexane-2,-6-dicarboxylate (2) Hydrochloride Salt A solution of the compound prepared as described in Example 3 (2.41 g) in diethyl ether (75 mL) was stirred at room temperature as gaseous hydrochloric acid was passed over the surface of the solution until no further salt formation occurred. After an additional five minutes, the salt was removed by filtration, washed with cold diethyl ether, and dried in vacuo at 60° C. for about 18 hours, to give 2.75 g of the title compound. Melting point: 189–191° C.

FDMS: m/z=242 (M+H).

Analysis calculated for $C_{12}H_{20}ClNO_4$: C, 51.89; H, 7.26; N, 5.04. Found: C, 52.03; H, 7.48; N, 5.06.

EXAMPLE 6

(−)-Diethyl 2-Aminobicyclo[3.1.0]hexane-2,6-dicarboxylate (4)

A solution of the racemic mixture of compounds prepared as described in Example 3 (6.56 g) in ethyl acetate (100 mL) was treated with a solution of (+)-di-p-toluoyl-D-tartaric acid (12.0 g) in ethyl acetate (100 mL). After standing overnight at room temperature, the crystalline solid was removed by filtration and dried to give 14.7 g. Additional crystalline solid was obtained by cooling the filtrate to 0° C. The combined crystalline solids were dissolved in hot ethyl acetate, containing enough 2- propanol for complete dissolution. After cooling to 0° C., the crystalline solid was isolated by filtration, to give 2.3 g of a solid having an enantiomeric excess of ≥95%. The freebase form was obtained by partitioning the salt between aqueous sodium bicarbonate and ethyl acetate. The organic phase was separated, dried over potassium carbonate, filtered, and concentrated in vacuo to give 0.77 g of the title compound.

FDMS: m/z=242 (M+H).

Optical rotation: $\alpha_D$=−5.15° (c=1, EtOH).

Analysis calculated for $C_{12}H_{19}NO_4$: C, 59.74; H, 7.94; N, 5.81. Found: C, 59.68; H, 8.13; N, 5.58.

EXAMPLE 7

(+)-Diethyl 2-Aminobicyclo[3.1.0]hexane-2,6-dicarboxylate (5)

The mother liquors from Example 6 were combined and concentrated in vacuo. The acid addition salt was converted to the freebase by partitioning between aqueous sodium bicarbonate and ethyl acetate. The organic phase was separated, dried over potassium carbonate, and concentrated in vacuo to give 3.7 g of an oil. This oil was treated with (−)-di-p-toluoyl-L-tartaric acid (7.14 g) in ethyl acetate (100 mL). After standing overnight at room temperature, the crystals were collected by filtration and dried. The crystalline solids were dissolved in hot ethyl acetate, containing enough 2-propanol to effect complete dissolution. After cooling to 0° C., the crystals were isolated by filtration to give 2.25 g of the title compound, having an enantiomeric excess of ≧95%. The freebase form of the title compound was obtained substantially as described above, to give 0.74 g.

FDMS: m/z=242 (M+H).

Optical rotation: ($\alpha_D$=7.22° (c=1, EtOH).

Analysis calculated for $C_{12}H_{19}NO_4$: C, 59.74; H, 7.94; N, 5.31. Found: C, 59.81; H, 7.88; N, 5.76.

EXAMPLE 8

(+)-2-Aminobicyclo[3.1.0]hexane-2,6-dicarboxylic Acid (6)

A solution of the compound prepared as described in Example 6 (0.69 g) in tetrahydrofuran (10 mL) was treated with 1N sodium hydroxide (10 mL), and the resulting mixture vigorously stirred at room temperature. After several days, the title compound was isolated by anion-exchange chromatography (Bio-Rad AG1-X8), eluting with 50% acetic acid/water, to give 0.53 g of the title compound.

FDMS: m/z=186 (M+H).

Optical rotation: $\alpha_D$=21.32° (c=1, 1N HCl).

Analysis calculated for $C_8H_{11}NO_4 \cdot 1.25H_2O$: C, 46.26; H, 6.55; N, 6.74. Found: C, 46.68; H, 6.47; N, 6.49.

EXAMPLE 9

(−)-2-Aminobicyclo[3.1.0]hexane-2,6-dicarboxylic Acid (7)

The title compound was prepared substantially as described in Example 8 from the compound whose preparation is described in Example 7 (0.59 g). After several days, the title compound was isolated by anion-exchange chromatography (Bio-Rad AG1-X8), eluting with 50% acetic acid/water, to give 0.45 g of the title compound.

FDMS: m/z=186 (M+H).

Optical rotation: $\alpha_D$=−22.72° (c=1, 1N HCl).

Analysis calculated for $C_8H_{11}NO_4 \cdot H_2O$: C, 47.29; H, 6.45; N, 6.89. Found: C, 47.50; H, 6.62; N, 6.31.

EXAMPLE 10

(1SR,2SR,5RS,6RS) 2-Aminobicyclo[3.1.0]hexane-2,6-dicarboxylic Acid (8)

The title compound was prepared from (1SR,2SR,5RS,6RS) diethyl 2-aminobicyclo[3.1.0]hexane-2,6-dicarboxylate substantially as described in Examples 3 and 4.

EXAMPLE 11

(+)-Diethyl-2-Aminobicyclo[3.1.0]hexane-2,6-dicarboxylate, Hydrochloride

A stream of anhydrous HCl gas was passed over the surface of a 0° C. solution of the compound of Example 6 in anhydrous diethyl ether (75 mL) until the formation of white precipitate ceased. The resulting suspension was stirred at room temperature for 2 hours. The reaction mixture was then diluted with diethyl ether (100 mL) and the solid filtered under vacuum. The solid was washed with $Et_2O$ (250 mL) and dried under vacuum at 70° C. for 4 hours affording the title compound (2.32 g, 8.4 mmol) 77%. mp=138°–140° C. FDMS=242 $M^+$+1. Anal. calcd. for $C_{12}H_{20}NClO_4$: C,51.89;H,7.26;N,5.04. Found C,51.61;H,7.32;N,4.99. $[\alpha]_D$=+35.52.(c=0.09,$H_2O$).

EXAMPLE 12

(+)-[1R-(1a,1aα,1bβ,2b,5a,5aβ,6aα)]−1,1a,1 b,2,5,5a,6,6a-octahydro-6-2,5-methanocycloprop[a]indene-1-carboxylic acid, ethyl ester A slurry of carbethoxymethyl dimethylsulfonium bromide (8.46 g, 36.9 mmol) in 27 ml of acetonitrile at ambient temperature under nitrogen was treated with 1,8-diazabicyclo[5.4.0]undec-7-ene (5.52 ml, 36.9 mmol). After stirring for 1 h the resulting yellow mixture was treated with (3aR)-3aα,4,7,7aα-tetrahydro-4α,7α-methano-1H-inden-1-one (3.60 g, 24.6 mmol) as a solid in portions over 3 min. The brown reaction was allowed to stir at ambient temperature for 15 h. The reaction was quenched with 5% HCl (13 ml), diluted with brine (50 ml), and washed with methyl t-butyl ether (3×50 ml). The combined organic extracts were dried ($MgSO_4$), filtered, and concentrated in vacuo to a brown oil (5.98 g). Chromatography (100 g of flash silica gel, 8:1 then 2:1/hexanes:ethyl acetate) of the crude oil provided 5.0 g (88%) of the title compound as a colorless oil determined to be a single diastereomer by HPLC analysis: $[\alpha]_D^{25}$+112° (c 1.39, MeOH); Rf 0.55 (hexanes:ethyl acetate/2:1); IR ($CHCl_3$) 2982 (w), 2938 (w), 1720 (s), 1276 (m), 1185 (m), 1048 (w) $cm^{-1}$; $^1H$ NMR ($CDCl_3$) δ6.18 (dd, 1H, J=5.6, 2.9 Hz), 6.07 (dd, 1H, J=5.6, 2.9 Hz), 4.14 (q, 2H, J=7.1 Hz), 3.24 (br s, 1H), 3.13 (br s, 1H), 2.86 (dd, 1H, J=6.9, 4.1 Hz), 2.64 (dd, 1H, J=6.9, 5.1 Hz), 2.21–2.16 (m, 2H), 1.88 (t, 1H, J=3.0 Hz), 1.57 and 1.37 (AB quartet, 2H, J=8.5 Hz), 1.26 (t, 3H, J=7.1 Hz); $^{13}C$ NMR ($CDCl_3$) δ213.31, 170.78, 135.59, 134.16, 61.56, 51.47, 51.17, 46.45 (2 carbons), 44.20, 39.76, 32.75, 25.76, 14.56. Anal. calcd. for $C_{14}H_{16}O_3$: C, 72.39; H, 6.94. Found: C, 72.63; H, 7.08.

EXAMPLE 13

(+)-[1(R),5(S),6(R)]-Bicyclo[3.1.0]hex-3-en-2-one-6-carboxylic acid ethyl ester.

A solution of the product of Example 12 (4.89 g, 21.1 mmol) in 14 ml of dry dimethyl sulfoxide was heated to reflux with simultaneous stirring and purging with nitrogen (sub-surface needle) to drive off liberated cyclopentadiene for 24 h. The reaction was cooled to room temperature, diluted with methyl t-butyl ether (100 ml), and washed with water (1×50 ml). The aqueous layer was washed with methyl t-butyl ether (1×25 ml) and the combined organic extracts were dried (MgSO$_4$), filtered, and concentrated in vacuo to a light yellow solid. The crude cyclopentenone was crystallized from hexanes-methyl t-butyl ether to afford 1.91 g (55%) of the title compound: mp 96°–98 ° C.; $[\alpha]_D^{25}$+251° (c 1.12, MeOH); Rf 0.49 (hexanes:ethyl acetate/2:1); IR (KBr) 2997 (w), 1728 (s), 1747 (s), 1696 (s), 1292 (m), 1266 (s), 1190 (s), 1177 (s) cm$^{-1}$; $^1$H NMR (CDCl$_3$) δ7.61 (dd, 1H, J=5.6, 2.5 Hz), 5.74 (d, 1H, J=5.6 Hz), 4.15 (q, 2H, J=7.1 Hz), 2.96–2.94 (m, 1H), 2.62 (br t, 1H, J=3.9 Hz), 2.26 (t, 1H, J=2.8 Hz), 1.27 (t, 3H, J=7.1 Hz); $^{13}$C NMR (CDCl$_3$) δ203.56, 168.28, 159.96, 129.99, 61.70, 46.19, 30.39, 29.28, 14.49. Anal. calcd. for C$_9$H$_{10}$O$_3$: C, 65.05; H, 6.07. Found: C, 64.78; H, 6.24.

EXAMPLE 14

(−)-[1(R),5(S),6(R)]-Bicyclo[3.1.0]hexan-2-one-6-carboxylic acid ethyl ester

A solution of the product of Example 13 (1.73 g, 10.4 mmol) in 35 ml of 95% ethanol under nitrogen was treated with 10% Pd/C (87 mg, 5 wt %). The flask was purged with hydrogen and stirring was maintained under a hydrogen atmosphere (balloon pressure) for 5 h at which time another 35 mg (2 wt %) of 10% Pd/C was added. The mixture was allowed to stir under hydrogen for an additional 50 min. The flask was purged with nitrogen and the catalyst was removed via filtration through celite, washing with ethyl acetate. The filtrate and washings were concentrated in vacuo to a yellow solid (1.75 g). The crude solid was crystallized from hexanes-methyl t-butyl ether to afford 1.38 g (79%) of the title compound: mp 63°–65° C.; $[\alpha]_D^{25}$ −60° (c 1.34, MeOH); Rf 0.49 (hexanes:ethyl acetate/2:1); IR (KBr) 2987 (w), 1722 (s), 1410 (m), 1193 (s), 1009 (m), 827 (m) cm$^{-1}$; $^1$H NMR (CDCl$_3$) δ4.16 (q, 2H, J=7.1 Hz), 2.52 (q, 1H, J=4.9 Hz), 2.29–2.22 (m, 2H), 2.17–2.00 (m, 4H), 1.28 (t, 3H, J=7.1 Hz); $^{13}$C NMR (CDCl$_3$) δ212.07, 170.80, 61.64, 36.17, 32.30, 29.59, 26.91, 22.87, 14.56. Anal. calcd. for C$_9$H$_{12}$O$_3$: C, 64.27; H, 7.19. Found: C, 64.10; H, 7.31.

EXAMPLE 15

(+)-[1(R),2(R),5(S),6(R),5'(R)]-2-Spiro-5'-hydantoinbicyclo[3.1.0]hexane-6-carboxylic acid ethyl ester A mixture of the produce of Example 14 (1.20 g, 7.13 mmol), potassium cyanide (511 mg, 7.85 mmol), and ammonium carbonate (1.37 g, 7.13 mmol) in 7.1 ml of 95% ethanol and 2.9 ml of water was allowed to stir at 36° C. for 10 h and at room temperature for 13 h. The cloudy yellow reaction was cooled to 0° C. and diluted with 7.8 ml of cold water. After stirring for 1.5 h the white solid was collected and washed with cold water (2×5 ml). The solid was dried in vacuo to provide 1.17 g (69%) of the title compound as a single diastereomer as determined by HPLC analysis: mp 247°–249° C.; $[\alpha]_D^{25}$+23° (c 1.05, MeOH); IR (KBr) 3504 (m), 3262 (m), 2983 (w), 2766 (w), 1771 (m), 1723 (s), 1415 (m), 1182 (w) cm$^{-1}$; $^1$H NMR (DMSO-d$_6$) δ10.58 (s, 1H), 7.93 (s, 1H), 4.06 (q, 2H, J=7.1 Hz), 2.08–2.01 (m, 1H), 1.94–1.83 (m, 4H), 1.79 (dd, 1H, J=13.9, 8.5 Hz), 1.40–1.33 (m, 1H), 1.20 (t, 3H, J=7.1 Hz); $^{13}$C NMR (DMSO-d$_6$) δ178.30, 172.62, 157.01, 69.52, 61.04, 33.86, 30.37, 28.27, 26.49, 20.95, 14.93. Anal. calcd. for C$_{11}$H$_{14}$N$_2$O$_4$: C, 55.46; H, 5.92; N, 11.76. Found: C, 55.76; H, 5.95; N, 11.84.

EXAMPLE 16

(−)-[1(R),2(R),5(S),6(R)]-2-Aminobicyclo[3.1.0]hexane-2,6-dicarboxylic acid

A solution of the product of Example 15 (976 mg, 4.10 mmol) in 8.2 ml of 3N NaOH was allowed to reflux with stirring for 24 h. Upon cooling to room temperature the reaction was applied directly to an ion exchange column (prepared from 50 g of Bio-Rad AG 1-X8 acetate resin prepared via washing with 50 ml of 1N NaOH followed by 50 ml of water followed by, after application of the reaction mixture, another 50 ml of 1N NaOH) eluting with 1:1/water:acetic acid, collecting 50 ml fractions. Fractions 2 and 3, which contained product, were combined and concentrated in vacuo providing 770 mg of a white solid. The solid was slurried in 4 ml of water and filtered, washing with water (1×4 ml). The solid was dried in vacuo at 40 ° C. to afford 634 mg (76%) of the title compound as a white powder: IR (KBr); 3235(br;s), 2971(m), 2016(br,w), 1694 (m), 1613(s), 1509(m), 1237(m) (cm–1). $^1$H NMR (trifluoroacetic acid-d) δ2.76–2.74 (m, 1H), 2.65–2.52 (m, 3H), 2.38–2.31 (m, 2H), 1.96–1.88 (m, 1H); $^{13}$C NMR (trifluoroacetic acid-d) δ179.43, 175.63, 69.53, 34.92, 31.75, 31.66, 27.63, 23.04. An analytical sample was prepared by crystallization from water: mp 277°–280 ° C. (dec); $[\alpha]_D^{25}$23° (c 1.35, 1N HCl)

EXAMPLE 17

2-Oxobicyclo[3.1.0]hexane-6-carboxylic acid

A mixture of 60 g of ethyl 2-oxobicyclo[3.1.0]hexane-6-carboxylate and 300 ml of 1N sodium hydroxide was stirred at 25°–30° C. After 2.5 hours, concentrated hydrochloric acid was added to adjust the pH to 0.8–1.2. The resulting solution was extracted with ethyl acetate. The extracts were dried over magnesium sulfate, filtered, and concentrated to give 49.1 g (98%) of the crude material. Recrystallization from 100 ml of ethyl acetate gave the title compound, mp 123.5°–128° C.

FDMS: m/z=140 (M+)

Analysis calculated for C$_7$H$_8$O$_3$: C, 60.00; H, 5.75. Found: C, 60.14; H, 5.79.

EXAMPLE 18

2-Oxobicyclo[3.1.0]hexane-6-carboxylic acid salt with (S)-1-phenylethylamine

A solution of 14 g of the compound prepared in Example 17 in 140 ml of 25% ethanol in ethyl acetate was combined with (S)-1-phenylethylamine (1 eq.). After stirring overnight, the precipitated salt was isolated by filtration and dried to give 11.87 g (45.4%) of the desired salt. Conversion of the salt to the partially resolved 2-oxobicyclo[3.1.0]hexane-6-carboxylic acid by the method of Example 17 and analysis indicated that the salt was 68% ee. The enantiomeric excess was determined by conversion to the methyl ester with diazomethane followed by chiral HPLC on a Chiralpak AS column at 40° C. eluted with 10% isopropanol/90% hexane at 1 ml/min with detection at 210 nm.

EXAMPLE 19

(+)-2-Oxobicyclo[3.1.0]hexane-6-carboxylic acid

A mixture of 1.31 g of the product of Example 18 and 10 ml of 1N hydrochloric acid was stirred for 5 minutes and extracted with ethyl acetate. The extracts were dried over sodium sulfate, filtered, and concentrated to give 0.61 g of the title compound, mp 110°–115° C. The product was determined to be 68% ee by chiral HPLC (method of Example 18)

FDMS: m/z=141 (M+H)

Optical Rotation: $\alpha_D$=49.85°

EXAMPLE 20

(−)-2-Spiro-5'-hydantoinbicyclo[3.1.0]hexane-6-carboxylic acid

A solution of the compound prepared as described in Example 19 (68% ee, 1 eq.), potassium cyanide (1.25 eq.), and ammonium carbonate (2.5 eq) were combined and stirred in ethanol/water at 25° C. for 40 hours. The mixture was acidified with 6N hydrochloric acid, concentrated, diluted with water, and filtered to give a 79% yield of a 90:10 mixture of diastereomers, mp 286°–290° C. The diastereomeric mixture was recrystallized from isopropanol/water to give in 48% yield the title compound in 100% diastereomeric and 100% enantiomeric purity (enantiomeric ratio determined by chiral HPLC on a 4.6×150 mm Chiralcel OD-H column, eluted with 15% isopropanol/85% hexane at 1 ml/min at 40° C. with detection at 220 nm; diastereomeric ration determined by HPLC on a Zorbax SB-phenyl column at 40° C. with elution with 90:10 buffer/acetonitrile eluted at 2 ml/min with detection at 220 nm (buffer=0.1M dibasic sodium phosphate monohydrate adjusted to pH 2.1 with phosphoric acid).

FDMS: m/z=211 (M+H)

Optical Rotation: $\alpha_D$=−25.98°

Analysis calculated for $C_9H_{10}N_2O_4$: C, 51.43; H, 4.79; N, 13.33. Found: C, 51.38; H, 4.80; N, 13.26.

EXAMPLE 21

Ethyl 2-spiro-5'-hydantoinbicyclo[3.1.0]hexane-6-carboxylate

A mixture of 5.05 g of ethyl 2-oxobicyclo[3.1.0]hexane-6-carboxylate, 2.15 g of potassium cyanide, 5.77 g of ammonium carbonate, 30 ml of 2B-3 ethanol, and 12 ml of water was stirred at 35° C. until the reaction was complete by HPLC.

After 15 hours, the reaction mixture was cooled to 0° C. and 33 ml of water was added to the mixture. After 2 hours at 0° C., the precipitate was isolated by filtration and dried to give 5.23 g (73%) of the title compound, mp 217°–220° C.

FDMS: m/z=238.1 (M+)

Analytical calculated for $C_{11}H_{14}N_2O_4$: C, 55.46; H, 5.92; N, 11.76. Found: C, 55.74; H, 5.88; N, 11.50.

EXAMPLE 22

2-Spiro-5'-hydantoinbicyclo[3.1.0]hexane-6-carboxylic acid

A mixture of 16.32 g of the product of Example 21 and 137 ml of 2N NaOH was stirred at 25° C. After 1 hour, concentrated hydrochloric acid was added to adjust the pH to 1.0. The resulting precipitate was isolated by filtration and dried to give 13.70 g (95%) of the title compound, mp 277°–279° C.

FDMS: m/z=210.1 (M+)

Analysis Calculated for $C_9H_{10}N_2O_4$: C, 51.43; H, 4.79; N, 13.33. Found: C, 51.70; H, 4.93; N, 13.43.

EXAMPLE 23

2-Spiro-5'-hydantoinbicyclo[3.1.0]hexane-6-carboxylic acid, (S)-1-phenylethylamine salt A mixture of 1.05 g of the product of Example 22 and 16.6 ml of a 1.6:1 solution of acetone:water was stirred at 25° C. while adding 1.53 g of R-(+)-1-phenylethylamine. The mixture was stirred for 2 hours at room temperature. The crystals were filtered, rinsed with acetone, and dried to give 0.74 g (45%) of the title compound, mp 205°–212°° C.

Optical Rotation: $\alpha_D$=−31.88° (c=1, methanol)

EXAMPLE 24

(−)-2-Spiro-5'-hydantoinbicyclo[3.1.0]hexane-6-carboxylic acid

A mixture of 0.74 g of the product of Example 23 and 10 ml of water was stirred at 25° C. while the pH was adjusted from 6.81 to 1.0 using 1N HCl. The reaction mixture was stirred for 1 hour and the product was collected by filtration and dried to give 0.35 g (75%) of the title compound, mp 310° C. (decomp).

FDMS: 210.1 (M+)

Optical Rotation: $\alpha_D$=−24.22° (c=1, methanol)

Analysis calculated for $C_9H_{10}N_2O_4$: C, 51.43; H, 4.80; N, 13.33. Found: C, 51.67; H, 4.87; N, 13.61.

EXAMPLE 25

(+)-2-Aminobicyclo[3.1.0]hexane-2,6-dicarboxylic Acid

A solution of 184 g of (−)-2-spiro-5'-hydantoinbicyclo[3.1.0]hexane-6-carboxylic acid and 1750 ml of 3N NaOH was heated at reflux until the reaction was complete by HPLC. After 28 hours, the solution was cooled to room temperature and filtered through glass paper to remove trace amounts of insoluble material. The pH of the solution was adjusted to 3.0 using concentrated HCl. The reaction mixture was stirred 1 hour at room temperature and two hours at 0° C. The precipitated product was collected by filtration, washed with 170 ml of cold water and dried to give 152.5 grams (86%) of the title compound.

FDMS: m/z=186.1 (M+)

Optical rotation: $\alpha_D$=23.18° (c=1, 1N HCl)

We claim:

1. A compound of the formula

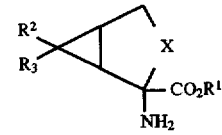

wherein:

X is $(CH_2)_n$;

$R^2$ is $CO_2R^4$ and $R^3$ is hydrogen, or $R^2$ is hydrogen and $R^3$ is $CO_2R^4$;

$R^1$ and $R^4$ are independently hydrogen, $C_1$–$C_{10}$ alkyl, $C_2$–$C_{10}$ alkenyl, aryl, or arylalkyl; and n is 1;

or a pharmaceutically-acceptable salt thereof.

2. The compound of claim 1 wherein $R^2$ is $CO_2R^4$ and $R^3$ is hydrogen; or a pharmaceutically-acceptable salt thereof.

3. The compound of claim 2 wherein $R^1$ and $R^4$ are independently hydrogen, $C_1$–$C_6$ alkyl, aryl, or arylalkyl, or a pharmaceutically-acceptable salt thereof.

4. The compound of claim 2, or a pharmaceutically-acceptable salt thereof, having the relative stereochemical configuration as shown below:

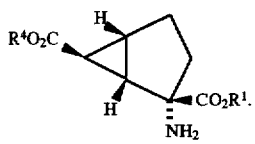

5. The compound of claim 4 wherein $R^1$ and $R^4$ are independently hydrogen, $C_1$–$C_4$ alkyl, arylalkyl, or aryl, or a pharmaceutically-acceptable salt thereof.

6. The compound of claim 5 wherein $R^1$ and $R^4$ are independently hydrogen, or $C_1$–$C_4$ alkyl, or a pharmaceutically-acceptable salt thereof.

7. The diastereomeric compound of claim 5 which is (1SR,2SR,5RS,6SR) 2-aminobicyclo[3.1.0]hexane-2,6-dicarboxylic acid, or a pharmaceutically-acceptable salt thereof.

8. The stereoisomeric compound of claim 5, which is (+)-2-aminobicyclo[3.1.0]hexane-2,6-dicarboxylic acid, a $C_1$–C4 alkyl, aralkyl or aryl ester thereof or a pharmaceutically acceptable salt thereof.

9. The stereoisomeric compound of claim 8, which is (+)-2-aminobicyclo[3.1.0]hexane-2,6-dicarboxylic acid, a $C_1$–$C_4$ alkyl ester thereof, or a pharmaceutically acceptable salt.

10. The stereoisomeric compound of claim 9 which is (+)-2-aminobicyclo[3.1.0]hexane-2,6-dicarboxylic acid, or a pharmaceutically-acceptable salt thereof.

11. The stereoisomeric compound of claim 10 which is (+)-2-aminobicyclo[3.1.0]hexane-2,6-dicarboxylic acid.

12. A pharmaceutical formulation comprising a compound of claim 1 in combination with one or more pharmaceutically-acceptable carriers, diluents, or excipients.

13. A pharmaceutical formulation comprising the compound of claim 8 in combination with one or more pharmaceutically-acceptable carriers, diluents, or excipients.

* * * * *